United States Patent
Van Schijndel et al.

(10) Patent No.: US 9,173,587 B2
(45) Date of Patent: Nov. 3, 2015

(54) SENSE A PHYSIOLOGICAL RESPONSE

(75) Inventors: Nicolle Hanneke Van Schijndel, Eindhoven (NL); Tim Johannes Willem Tijs, Helmond (NL); Rachel Estelle Thilwind, Cambridge (GB); Martijn Krans, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 534 days.

(21) Appl. No.: 13/383,707

(22) PCT Filed: Jul. 16, 2010

(86) PCT No.: PCT/IB2010/053245
§ 371 (c)(1),
(2), (4) Date: Jan. 12, 2012

(87) PCT Pub. No.: WO2011/010255
PCT Pub. Date: Jan. 27, 2011

(65) Prior Publication Data
US 2012/0116298 A1 May 10, 2012

(30) Foreign Application Priority Data
Jul. 23, 2009 (EP) .................................. 09166201

(51) Int. Cl.
*A61M 1/06* (2006.01)
*A61B 5/053* (2006.01)

(52) U.S. Cl.
CPC ............... *A61B 5/0533* (2013.01); *A61M 1/06* (2013.01); *A61M 2230/06* (2013.01); *A61M 2230/08* (2013.01); *A61M 2230/18* (2013.01); *A61M 2230/50* (2013.01); *A61M 2230/60* (2013.01); *A61M 2230/63* (2013.01); *A61M 2230/65* (2013.01)

(58) Field of Classification Search
CPC ..... A61B 5/0531; A61B 5/0533; A61M 1/06; A61M 1/066; A61M 2230/08; A61M 2230/18; A61M 2230/50; A61M 2230/60; A61M 2230/63; A61M 2230/65
USPC .......................................... 604/73–76, 65–67
See application file for complete search history.

(56) References Cited

U.S. PATENT DOCUMENTS

| 4,290,460 A | 9/1981 | Deborde |
| 5,515,858 A * | 5/1996 | Myllymaki ................... 600/301 |
| 5,590,648 A | 1/1997 | Mitchell et al. |
| 6,516,289 B2 * | 2/2003 | David ............................ 600/384 |

(Continued)

FOREIGN PATENT DOCUMENTS

| EP | 1430918 A1 | 6/2004 |
| GB | 2378762 A | 2/2003 |

(Continued)

OTHER PUBLICATIONS

Akio Sato et al; "The Modulation of Visceral Functions by Somatic Afferent Activity", Dept. of Physiology, Japanese Journal of Physiology, No. 37, pp. 1-17—1987.

*Primary Examiner* — Theodore Stigell (57) ABSTRACT

An apparatus comprising a sensing unit configured to detect a physiological response from a user of a breast pump and to trigger a change in an operation of the breast pump in dependence of the detected physiological response, the sensing unit being located separately from a funnel of the breast pump.

14 Claims, 7 Drawing Sheets

(56) References Cited

U.S. PATENT DOCUMENTS

| | | |
|---|---|---|
| 7,329,247 B2 | 2/2008 | Wallace |
| 7,641,629 B2 * | 1/2010 | Yuen ................................ 604/74 |
| 2002/0148407 A1 * | 10/2002 | Brown et al. ............. 119/14.02 |
| 2004/0122357 A1 * | 6/2004 | Kent et al. ........................ 604/74 |
| 2004/0122358 A1 * | 6/2004 | Kent et al. ........................ 604/74 |
| 2004/0133151 A1 * | 7/2004 | Watanabe ........................ 604/74 |
| 2005/0059928 A1 * | 3/2005 | Larsson .......................... 604/74 |
| 2005/0228342 A1 * | 10/2005 | Yuen ................................ 604/74 |
| 2005/0234370 A1 * | 10/2005 | Beal et al. ....................... 601/15 |
| 2006/0106334 A1 * | 5/2006 | Jordan et al. ................... 604/74 |
| 2007/0010760 A1 * | 1/2007 | Rosenfeld .................... 600/573 |
| 2008/0177224 A1 | 7/2008 | Kelly et al. |
| 2008/0243060 A1 | 10/2008 | Hartmann et al. |
| 2009/0062731 A1 | 3/2009 | Keyong et al. |
| 2010/0016789 A1 * | 1/2010 | Bosshard et al. ............... 604/74 |
| 2010/0217148 A1 * | 8/2010 | Binder .......................... 600/547 |

FOREIGN PATENT DOCUMENTS

| | | |
|---|---|---|
| WO | 03066133 A1 | 8/2003 |
| WO | 2009081313 A1 | 7/2009 |

\* cited by examiner

SENSE A PHYSIOLOGICAL RESPONSE

FIELD OF THE INVENTION

The present invention relates to a sensing unit and method for detecting a physiological response and for triggering a change in an operation of a breast pump in dependence of the physiological response.

BACKGROUND TO THE INVENTION

An expression of milk from a female breast during breast feeding is preceded by a milk ejection reflex (MER), in which a contraction of the myoepithelial cells around milk glands in the breast forces milk to flow towards the nipple. Until an MER occurs, little or no milk will be expressed.

An MER is naturally instigated by the suckling action of a baby. After an MER has occurred, a baby will naturally alter its suckling action to one which encourages a continued flow of milk from the breast.

It is desirable that an artificial breast pump should not only be able to instigate an MER but should also be able to mimic the second stage of the natural suckling process by altering the type of stimulation provided to the breast after an MER has occurred. However, in order to implement the change in stimulation at the correct time, it is first necessary to detect when an MER has occurred.

SUMMARY OF THE INVENTION

According to an aspect of the invention, there is provided an apparatus comprising a sensing unit configured to detect a physiological response from a user of a breast pump and to trigger a change in an operation of the breast pump in dependence of the detected physiological response, wherein the sensing unit is located separately from a funnel of the breast pump.

When the funnel of the breast pump is located against the breast of the user, the sensing unit may be configured to detect said physiological response from a body part of the user other than the user's breast.

The sensing unit may be configured to detect a milk ejection reflex on the basis of the detected physiological response.

The sensing unit may be configured to trigger a change in the operation of the breast pump from a let-down mode to an expression mode in response to detecting a milk ejection reflex.

The sensing unit may be configured to detect a relaxation state of the user of the pump on the basis of the detected physiological response.

The sensing unit may be configured to trigger a change in the operation of the breast pump from a relaxation mode to a let-down mode in response to detecting a relaxed state of the user of the pump.

The sensing unit may be configured to trigger a change in the operation of the breast pump from a neutral mode to a relaxation mode in response to detecting a stressed state of the user of the pump.

The sensing unit may be configured to trigger a change in the operation of the breast pump from a let-down mode to a relaxation mode in response to detecting a stressed state of the user of the pump.

The sensing unit may comprise a sensor configured to detect said response.

The sensor may be an electrodermal sensor configured to detect said response from skin tissue of the user of the breast pump.

The physiological response may be a galvanic skin response.

The physiological response may be a pulse of the user.

The physiological response may be a respiration rate of the user.

The physiological response may be a body temperature of the user.

The physiological response may be a heart rate variability of the user.

The apparatus may comprise a glove in which the sensor is located.

The glove may comprise at least one finger receptacle and the sensor may be located in the at least one finger receptacle to contact skin tissue of a hand of the user when inserted into the receptacle.

The apparatus may comprise a container holder on which the sensor is located.

The sensor may be located at an exterior of the container holder to contact the skin tissue of the user's hand when holding the container holder.

The sensor may be located on a handle of the container holder.

The apparatus may comprise a bracelet on which the sensor is located.

The sensor may be located at an exterior of the bracelet to contact the skin tissue of the user when wearing the bracelet.

The apparatus may comprise the breast pump, and the breast pump may be configured to change its operation in response to receiving a signal from the sensing unit.

According to another aspect of the invention, there is provided a method for controlling the operation of a breast pump comprising detecting a physiological response from a user of the breast pump, the response being detected from a body part of the user other than the user's breast; and triggering a change in an operation of the breast pump in dependence of the detected physiological response.

Detecting the physiological response may occur whilst a funnel of the breast pump is located against a breast of the user of the pump.

The method may comprise detecting a milk ejection reflex on the basis of the detected physiological response.

The method may comprise detecting a relaxation state of the user.

The change in the operation of the breast pump may be from a let-down mode to an expression mode.

The change in the operation of the breast pump may be from a relaxation mode to a let-down mode.

The change in the operation of the breast pump may be from a let-down mode to a relaxation mode.

The change in the operation of the breast pump may be from a neutral mode to a relaxation mode.

The change in operation may be made in response to detecting a milk ejection reflex.

The change in operation may be made in response to detecting a relaxed state of the user.

The change in operation may be made in response to detecting a stressed state of the user.

The method may comprise detecting said response from skin tissue of the user of the breast pump.

The skin tissue may be skin tissue of the hand, wrist or foot of the user of the breast pump.

The physiological response may be a galvanic skin response.

The method may further comprise changing the operation of the breast pump.

These and other aspects of the invention will be apparent from and elucidated with reference to the embodiments described hereinafter.

DETAILED DESCRIPTION OF EMBODIMENTS

Embodiments of the invention will now be described, with reference to the accompanying figures.

Figure 1:
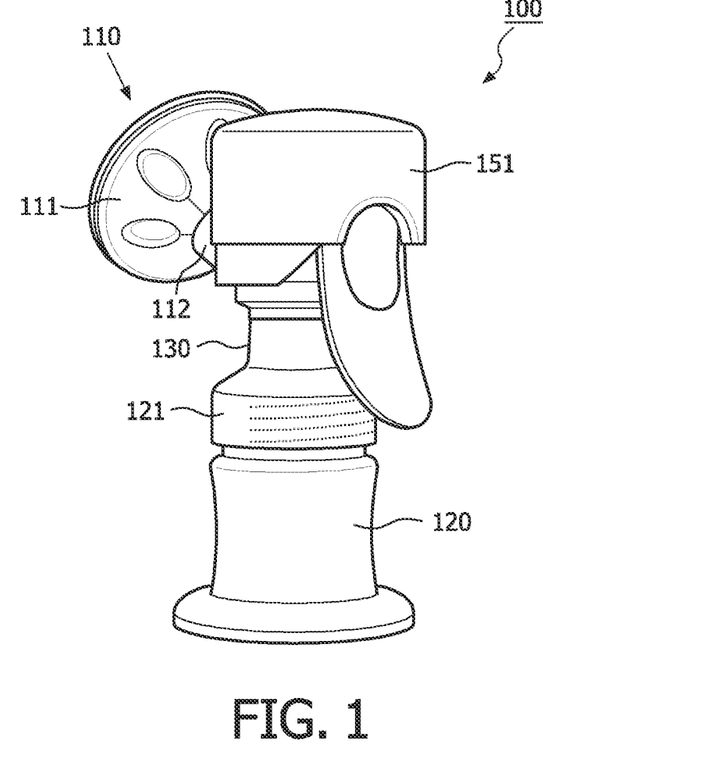
FIG. 1 is an illustration of a breast pump having a funnel connected to a container via a connection pipe.

Referring to FIG. 1, a breast pump 100 comprises a funnel 110 and a container 120. The funnel 110 and container 120 are connected by a connection pipe 130, which may be substantially tubular in form.

As can be seen from FIG. 1, the funnel 110 comprises an inlet portion 111 and an outlet portion 112. The inlet portion 111 may take the form of a hollow truncated cone such that it can be comfortably received on a female breast to collect milk expressed from the breast's nipple. The outlet portion 112 may take the form of a fluid-tight exit tube, which is coupled to the connection pipe 130 to allow milk expressed from the breast to be channeled from the inlet portion 111 of the funnel 110 towards the container 120.

The connection pipe 130 provides a fluid-tight passageway between the funnel 110 and the container 120 to convey milk expressed from the breast into the container 120 without leakage. The container 120 may comprise any fluid-tight container suitable for containing breast milk, for example a suitable plastics container. An inlet 121 of the container 120 may be coupled to the connection pipe 130 by a screw fit to ensure that the container 120 does not become undesirably detached from the connection pipe 130 when the breast pump 100 is in use. Use of a screw fit coupling allows the container 120 to be separated from the connection pipe 130 when desired, for example in order to empty the container 120 of breast milk.

A similar screw fit coupling may be provided between the connection pipe 130 and the outlet portion 112 of the funnel 110. However, the funnel 110 and the connection pipe 130 may alternatively be integrally formed such that the connection pipe 130 comprises part of the funnel 110. For example, the funnel 110 and the connection pipe 130 may comprise a single plastics moulding which screws directly to the inlet 121 of the container 120. This is shown in FIG. 1.

Figure 2:
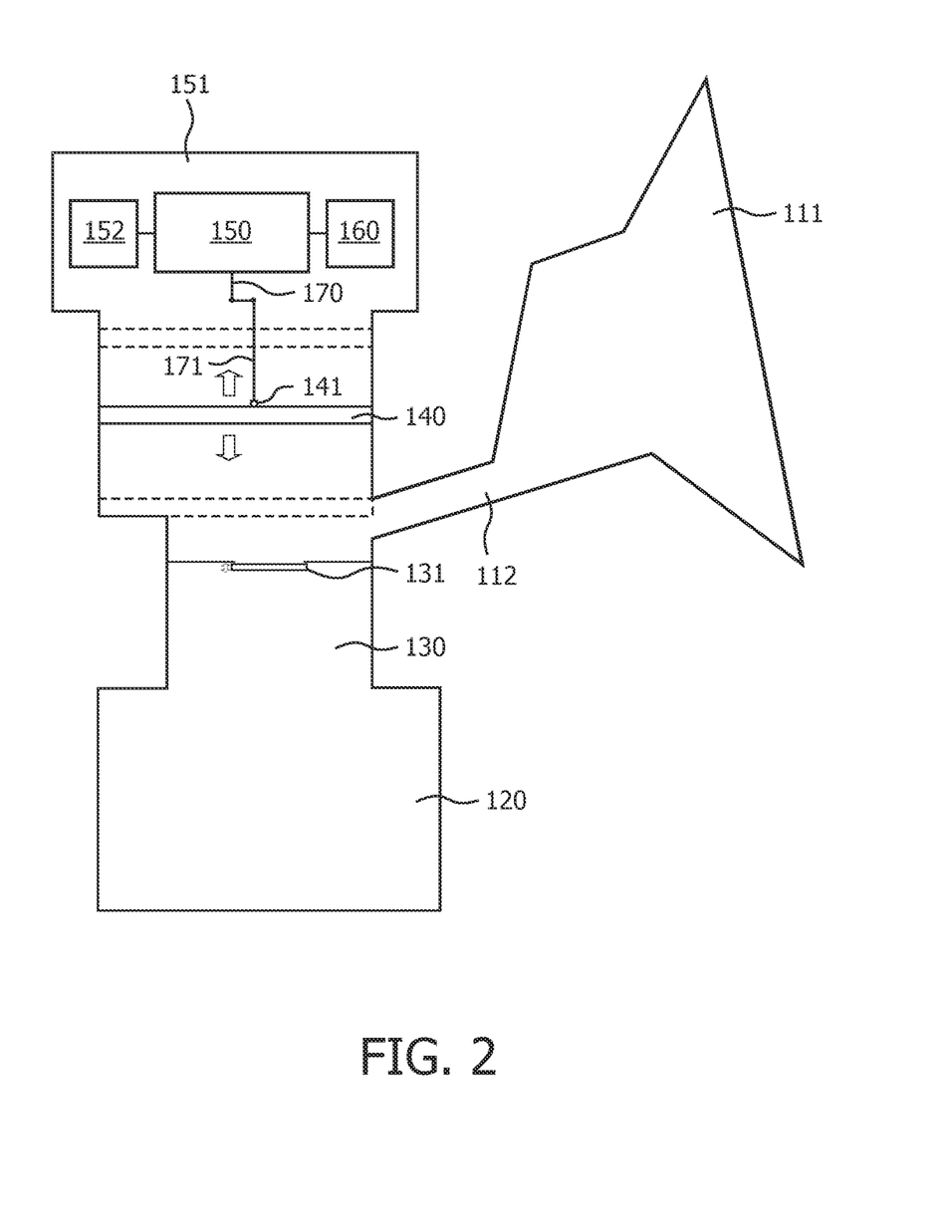
FIG. 2 is a diagram of the breast pump shown in FIG. 1. An actuatable diaphragm and valve are shown in the connection pipe for varying an internal volume of the breast pump.

The connection pipe 130 may comprise a diaphragm 140 which can be actuated to vary the internal volume of the connection pipe 130. The internal volume of the connection pipe 130 excludes the internal volume of the funnel 110 and comprises the internal volume defined by the walls of the connection pipe 130, the actuatable diaphragm 140 and the valve 131 (discussed below) at the boundary between the connection pipe 130 and the container inlet 121. In the example shown in FIG. 2, the diaphragm 140 forms a roof of the connection pipe 130. Actuation of the diaphragm 140 in an upwards direction increases the internal volume of the connection pipe 130, whilst actuation of the diaphragm 140 in a downwards direction decreases the internal volume of the connection pipe 130. The actuation of the diaphragm 140 is illustrated in FIG. 2 by the arrows showing the upwards and downwards motion, and by the dotted extreme upwards and downwards positions of the diaphragm 140. It will be understood that a rapid increase in the internal volume of the connection pipe 130 will cause a decrease in the air pressure inside the breast pump 100, thereby causing the inlet portion 111 of the funnel 110 to clamp against the skin tissue of the breast. A valve 131 may be provided in the connection pipe 130 adjacent to the inlet 121 of the container 120 in order to seal the fluid channel between the connection pipe 130 and the container 120. The valve 131 is configured to close when the diaphragm 140 is actuated in an upwards direction to decrease the air pressure inside the connection pipe 130. This is shown by the arrow in FIG. 2. It will be appreciated that by isolating the air inside the container 120 from the air inside the funnel 110, the valve 131 serves to increase the difference between the external air pressure and internal funnel pressure caused by actuation of the diaphragm 140, and thereby causes the inlet 111 of the funnel 110 to clamp more securely against the breast tissue.

The diaphragm 140 may be coupled to an actuator 150 which is configured to move the diaphragm 140 in both of the upwards and downwards directions referred to above, thereby respectively increasing and decreasing the internal volume of the connection pipe 130. The actuator 150 may comprise an electric motor 150 located on the breast pump 100, for example in a head unit 151 located directly above the connection pipe 130. This allows the electric motor 150 to be coupled with the diaphragm 140, as discussed below. The electric motor 150 may be driven by a power source 160, such as a battery pack 160 provided adjacent the electric motor 150 in the head unit 151. Alternatively, the electric motor 150 may be mains powered, for example using a power lead to connect the electric motor 150 to a mains power supply via an appropriate transformer unit.

The electric motor 150 may be coupled to a drive mechanism 170, which comprises an arm 171 configured to actuate the diaphragm 140 to vary the internal volume of the breast pump 100. For example, the arm 171 may comprise an end portion which is shaped to provide a locking configuration between the arm 171 and a nipple portion 141 on an upper surface of the diaphragm 140. When the electric motor 150 is driven, the drive mechanism 170 may cause the arm 171 to move longitudinally back and forth within the connection pipe 130 so as to actuate the diaphragm 140 upwards and downwards and thereby cause the internal volume of the connection pipe 130 to be respectively increased and decreased.

As discussed above, when the inlet 111 of the funnel 110 is positioned against the skin tissue of a female breast, a decrease in the internal air pressure of the breast pump 100 caused by actuation of the diaphragm 140 will cause the funnel 110 to clamp against the skin tissue of the breast and the valve 131 in the connection pipe 130 to close. Once the valve 131 is closed, further actuation of the diaphragm 140 to decrease the air pressure inside the funnel 110 causes the breast tissue to be drawn into the funnel's inlet 111. The air pressure inside the funnel 110 can be increased again by actuating the diaphragm 140 in the opposite direction to reduce the internal volume of the connection pipe 130, thereby allowing the breast tissue to revert to its normal shape.

A cycle may be instigated in which the electric motor 150 drives a repeated backward and forward longitudinal motion of the arm 171 to actuate the diaphragm 140 upwards and downwards inside the connection pipe 130. In the discussion below, one complete cycle will be taken as meaning a movement of the diaphragm 140 from a starting position to an upper position, then to a lower position, then back to the starting position. During the cycle the air pressure inside the funnel 110 will continually vary, thereby causing breast tissue positioned against the funnel 110 to repeatedly move into and out of the inlet 111. Such a cycle may be used to provide a stimulating effect to the breast. The cycle may be optimized to mimic the suckling action of a baby and cause milk to be expressed into the breast pump 100, or to help relax the user of the pump. This is discussed in more detail below.

The frequency at which the diaphragm 140 moves up and down can be measured in the number of complete cycles that the diaphragm 140 completes during a fixed period of operation of the breast pump 100. Similarly, the (peak to peak) amplitude with which the diaphragm 140 moves can be measured as the distance between the extreme upper and lower positions of the diaphragm 140 during a particular cycle. These positions do not necessarily correspond to the extreme positions of the diaphragm 140 shown in FIG. 2. For example, the extreme upper and lower positions of the diaphragm 140 during any particular cycle may be respectively lower and higher than the extreme positions shown in FIG. 2. A variation in either the frequency or the amplitude with which the diaphragm 140 is actuated by the driving mechanism 170 may vary the stimulating effect provided to the breast by the breast pump 100. This allows the stimulating effect provided by the breast pump 100 to be tailored for a particular user of the pump 100 by controlling an input signal to the electric motor 150 which drives movement of the diaphragm 140. The stimulating effect can also be optimized in order to mimic different stages of the natural suckling process, and to help relax the user of the pump 100.

The breast pump 100 may be operable in different stimulation modes, and may be configured to switch between these modes in response to sensing one or more physiological responses from a user of the pump 100. For example, one mode of operation may comprise a let-down mode in which the frequency and amplitude of the diaphragm cycle are optimized to instigate an MER, whilst another mode of operation may comprise an expression mode in which the frequency and amplitude of the diaphragm cycle are optimized to encourage a continued expression of milk from the nipple after an MER has occurred. Another mode of operation may comprise a relaxation mode in which the frequency and amplitude of the diaphragm cycle are optimized to provide a relaxing effect on the skin tissue of the user, thereby helping to instigate an MER and/or aid with the expression of milk. Another mode of operation may comprise a neutral mode in which the diaphragm 140 is either inactive or the frequency and amplitude of the diaphragm cycle are such as to provide a relatively slow, low suction pumping action. The breast pump 100 may be configured to switch from a first of any of the operational modes described above to a second of any of the other operational modes described above in response to sensing a physiological response from the user of the pump 100. As will be described below, a switch between operational modes may, for example, comprise a switch from the let-down mode to the expression mode in response to receiving a trigger signal indicating that an MER has occurred. A switch between different operational modes may alternatively comprise a switch from the neutral mode or let-down mode to the relaxation mode or from the relaxation mode to the let-down mode or expression mode. A person skilled in the art will appreciate that whilst the differences between the different stimulation modes are described here in terms of differences in the frequency and amplitude of the diaphragm cycle, a transition between the first and second modes may additionally or alternatively involve an adjustment of other parameters of the breast pump 100. For example, the breast pump 100 may be provided with massage pads on the interior surface of the inlet 111 of the funnel 110 which are configured to massage the skin tissue of the breast when the breast pump 100 is in use. The massaging effect provided by the massage pads may vary depending on the mode of operation, for example in order to encourage a milk ejection reflex (let-down mode), a continued expression of milk (expression mode) or to relax the user (relaxation mode).

Figure 3:
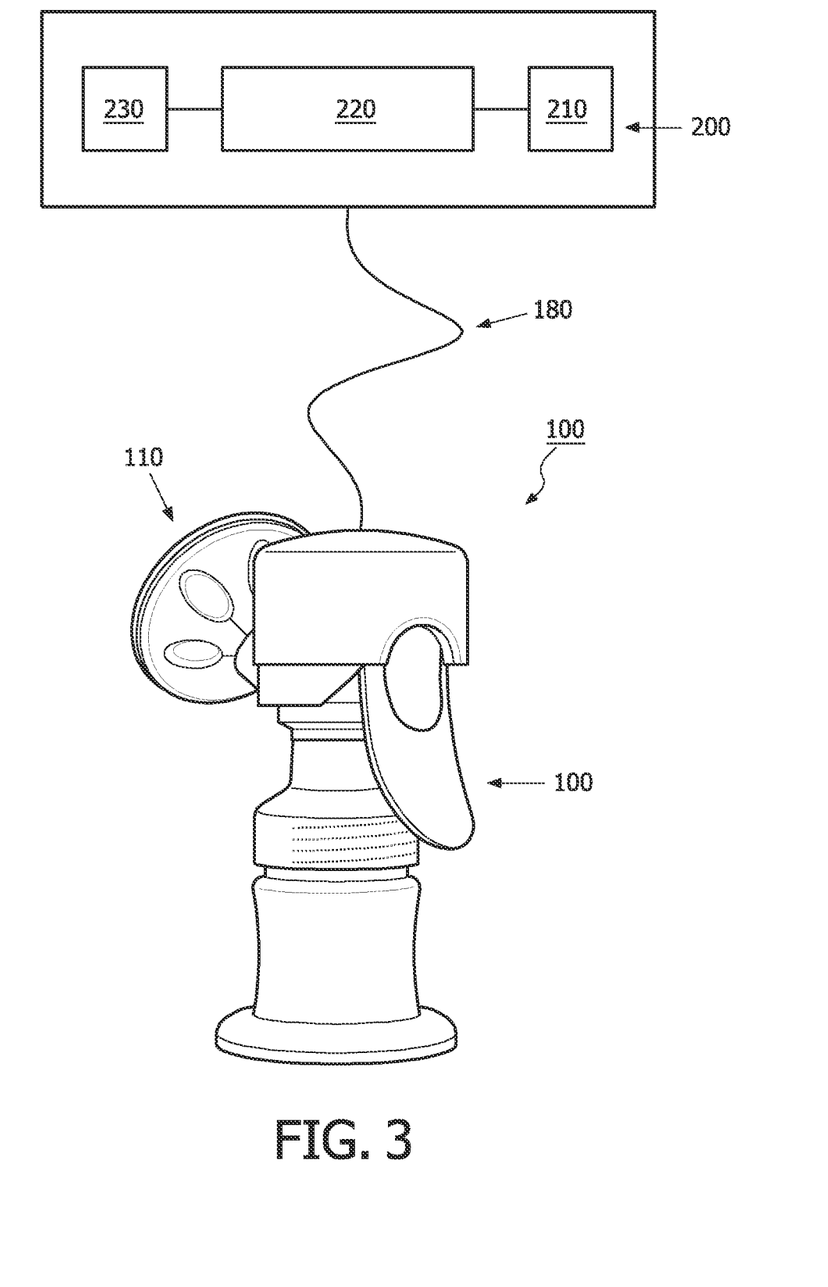
FIG. 3 is a block diagram of a sensing unit connected to a breast pump by a communication lead.
Figure 4A:
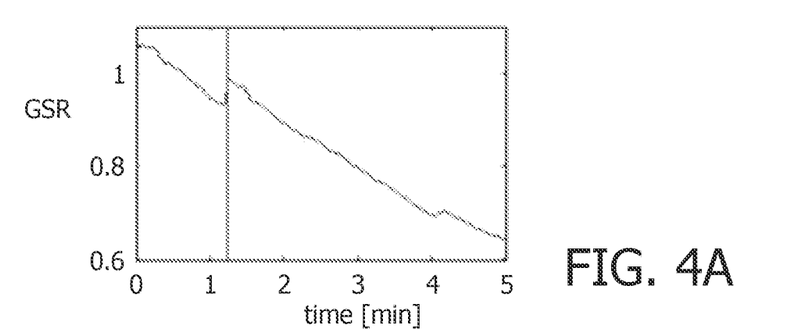
FIGS. 4A to 4D are graphical plots showing how a galvanic skin response of a user of a breast pump varies with time before, during and after a milk ejection reflex.
Figure 4B:
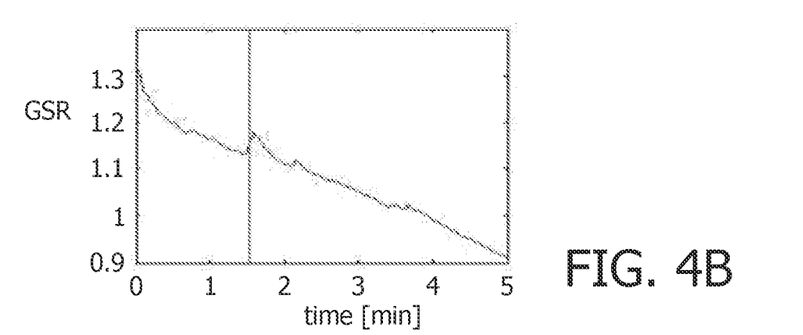
Figure 4C:
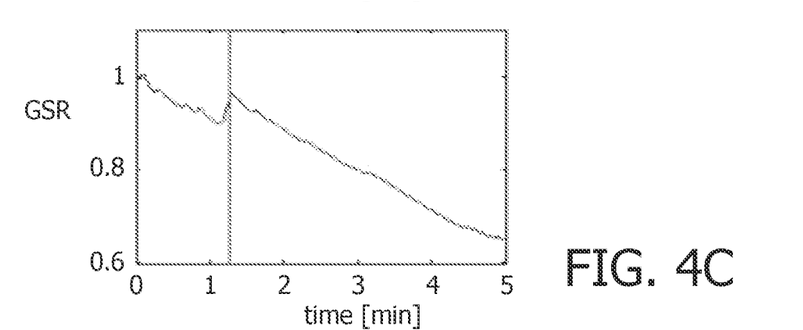
Figure 4D:
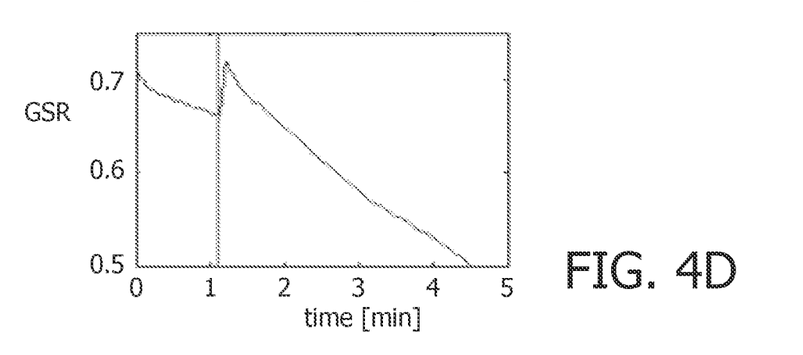

Referring to FIG. 3, a sensing unit 200 located separately and remotely from the funnel 110 of the breast pump 100 may be configured to sense a physiological response from a user of the pump 100 and to detect a condition of the user on the basis of the sensed response. For example, the sensing unit 200 may be configured to detect a milk ejection reflex (MER) (or let-down reflex) in the breast of a user of the breast pump 100. In response to detecting a condition of the user, the sensing unit 200 may be configured to generate a trigger signal for changing the operational mode of the breast pump 100 from a first of the operational modes described above to a second of the operational modes. For example, in the case of the sensing unit 200 detecting an MER, the sensing unit 200 may be configured to generate a trigger signal for changing the operational mode of the pump 100 from the let-down mode to the expression mode. In the case of the sensing unit 200 detecting that the user of the pump 100 is stressed, the sensing unit 200 may be configured to generate a trigger signal for changing the operational mode of the pump 100 from the let-down mode or neutral mode to the relaxation mode. In the case of the sensing unit 200 detecting that the user of the pump 100 is relaxed, the sensing unit 200 may be configured to switch the operational mode of the pump from the relaxation mode to the let-down mode.

The pump 100 may be configured such that the different operational modes may operate either singly or together in a simultaneous fashion. For example, the relaxation mode may operate in tandem with the let-down mode.

The term physiological response is used here to include any measurement, reading or change in a physiological state of the user of the breast pump 100. The physiological responses may be detected from the skin tissue of the user of the breast pump 100. The sensing unit 200 may be configured to detect the physiological responses from a part of the user's body other than the user's breast tissue. In one example, the detection of whether an MER has occurred is achieved by comparing the sensed physiological responses with stored physiological responses which are known to be indicative of an MER. A detection of the user being stressed or relaxed, or a detection of any other condition of the user, can be achieved in the same way, i.e. by comparing sensed physiological responses with stored physiological responses which are known to be indicative of stress. Alternatively, the detection of a condition can be achieved using a computer model, for example employing an appropriate algorithm, to analyze the signals from the sensors 210 and to search for events that are indicative of particular conditions. These events could, for example, comprise peaks or troughs in the signals from a particular type of sensor 210. An example of this is discussed below in relation to FIGS. 4A to 4D. The stored physiological responses and/or the computer model may be stored in a storage unit 230 of the sensing unit 200, such as a suitable semiconductor memory device. Upon detecting a condition, such as an MER or a stressed/relaxed state of the user, the sensing unit 200 may be configured to generate and send the trigger signal referred to above to the breast pump 100. The trigger signal may be generated when the physiological responses sensed by the sensing unit 200 are within predetermined limits of the stored physiological responses indicative of an MER, a stressed state of the user of the pump 100 or a relaxed state of the user of the pump 100. The predetermined limits may be stored in the storage unit 230.

The comparison between the sensed and stored physiological responses, and/or the execution of the computer model, may be performed in a control unit 220, as is described in more detail below. The breast pump 100 may be configured to respond to receiving the trigger signal by switching its operation from a first of the operational modes to a second of the operational modes mode, as described above, for example by varying the frequency and/or amplitude of the cyclic motion of the diaphragm 140.

The sensing unit 200 comprises at least one physiological sensor 210. For example, the sensing unit 200 may comprise a physiological sensor 210 comprising an electro-dermal sensor configured to contact the skin tissue of a user of the breast pump 100 when the breast pump 100 is in use. The electro-dermal sensor 210 may comprise a pair of electrodes configured, for example, to measure an electrical resistance from the skin tissue with which the electrodes are in contact. The electro-dermal sensor 210 may therefore be used to detect a galvanic skin response (GSR) from the user of the breast pump 100, as is described below. The sensing unit 200 may additionally or alternatively comprise other types of physiological sensors 210, such as a cardio-respiratory sensor 210 which can be used to detect the user's pulse, body temperature, rate of respiration or blood pressure, or to perform an electrocardiogram (ECG). Another type of physiological sensor 210 may be a somatomotor sensor 210, which may be configured to perform an electro-myogram or electro-oculogram, or used to detect changes in the user's eye pupil size, frequency of eye blinks and/or length of eye blinks. A further type of physiological sensor 210 may be an endocrine sensor 210, which can be used to measure the level of oxytocin in the user's body. The equipment for taking such measurements is well-understood and so will not be described in more detail here.

The sensing unit 200 may further comprise a control unit 220 which is coupled to each of the physiological sensors 210 and configured to receive signals from the sensors 210 which are indicative of physiological responses of the user's body. For example, the control unit 220 may be electrically connected to each of the sensors 210 via electrical wires extending between the control unit 220 and the sensors 210, which are used to convey signals from the sensors 210 to the control unit 220. The control unit 220 may be configured to analyze the signals received from the sensors 210 and to determine one or more physiological responses of the user of the breast pump 100. For example, referring to FIG. 3, the control unit 220 may be configured to detect electro-dermal responses such as galvanic skin response (GSR) from analysis of the electric potential at the electrode sites. The control unit 220 may additionally or alternatively be configured to detect other types of physiological response, such as the user's body temperature, blood pressure, pulse, heart rate variability, relaxation state, changes in the user's eye pupil size and the frequency and/or length of eye blinks. However, it will be appreciated that the physiological responses may alternatively be detected directly by the physiological sensors 210 and fed directly to the control unit 220.

As discussed above, the control unit 220 may be configured to compare the physiological responses determined via the sensors 210 with stored physiological responses which may be indicative of an MER, a stressed state of the user of the pump 100, a relaxed state of the user of the pump 100 or another condition. Additionally or alternatively, the control unit 220 may be configured to input the signals from the sensors 210 to a computer model, which is executed by the control unit 220 to determine events indicative of a particular condition (e.g. an MER, relaxed/stressed state) of the user of the pump 100. The stored responses and/or computer model may be pre-loaded into a storage unit 230 of the sensing unit 200, and may be accessed by the control unit 220 during operation of the breast pump 100. Optionally, the sensing unit 200 may be configured to select one of a plurality of different stored responses for use in the detection of the MER. The sensing unit 200 may additionally or alternatively be configured to select one or a plurality of different stored responses for use in the detection of a stressed or relaxed state of the user of the pump 100. The selection of the stored response by the sensing unit 200 may be based on the user of the breast pump 100. For example the selection may be based on physical attributes of the user such as height and weight, which can be input into the sensing unit 200 through an input means. The sensing unit 200 may also comprise means for fine tuning the stored responses to make them specific to the regular user of the pump 100. Such fine tuning could equally be applied to the computer model, for example by adjusting the parameters of the model based on the physical attributes of the user. In one example, the sensing unit 200 may be configured to store an average pumping time which is required to instigate an MER for a particular user, and to use the stored time to aid in the detection of an MER.

The control unit 220 may be configured to compare the sensed responses against the stored responses, and to generate a trigger signal indicating a particular condition of the user of the pump when the sensed responses are within pre-determined limits of the stored responses for that condition. Alternatively or additionally, the computer model described above can be used.

As previously explained, the trigger signal may, for example, indicate that an MER has taken place or that the user of the pump is in a stressed or relaxed state. FIGS. 4A to 4D show the GSR taken from the skin tissue on the hand of a milk-expressing female (when using the breast pump 100), measured using the sensing unit 200 discussed above. Each of the FIGS. 4A to 4D shows a GSR plotted against the time elapsed since the start of a milk-expressing action. The vertical lines on each of the plots indicate the point at which the female noted that an MER had occurred. As can be seen, the vertical lines correspond very closely with the peaks in the GSR. These peaks are taken as being indicative of an MER, and thus can be used by the sensing means 200 to detect when an MER has occurred. A stressed or relaxed state can be detected in a corresponding manner, i.e. by analysis of a GSR curve to identify points or trends indicative of a stressed or relaxed state. For example, referring to FIGS. 4A to 4D, the downward trend in the GSR curve after the occurrence of an MER indicates that the user of the pump 100 is becoming more relaxed as the milk-expressing session continues. A similar method may be used to identify conditions of the user from other types of physiological response, such as by analysis of the user's pulse, body temperature or heart rate variability.

Figure 5:
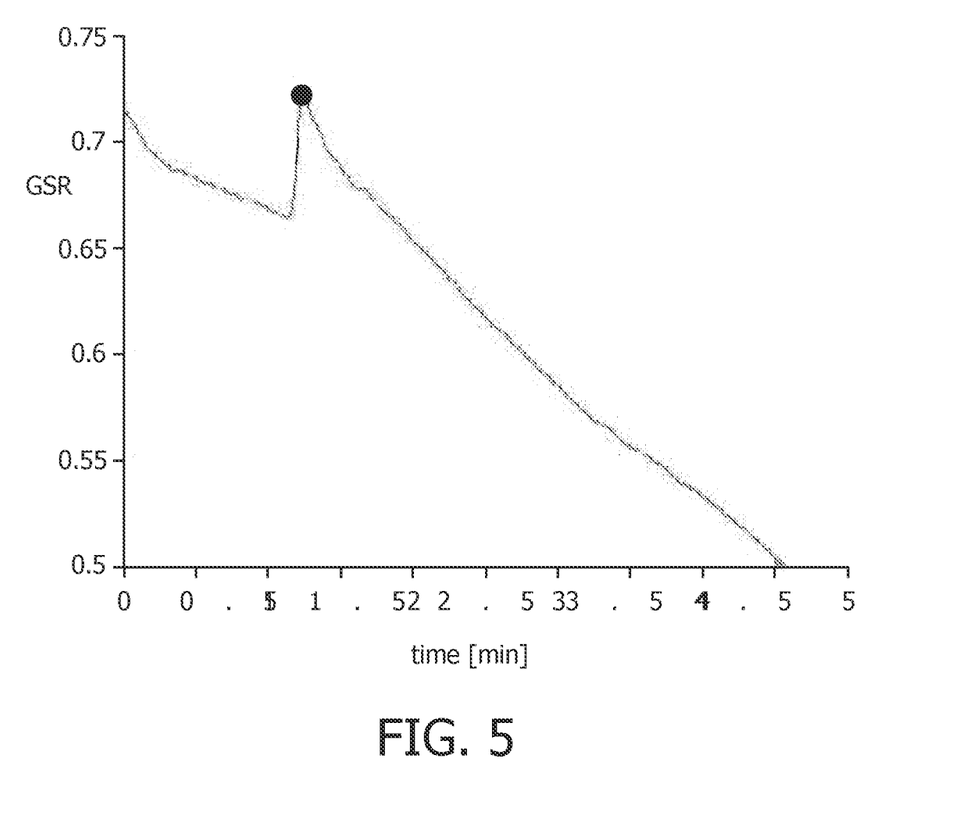
FIG. 5 shows the identification of a peak in the galvanic skin response of a user of a breast pump by a computer program.

Referring to FIG. 5, a computer algorithm or appropriate program loaded into the sensing means 200 may, when executed by a processor in the control unit 220, be configured to detect peaks or other points indicative of a particular condition of the user in a GSR reading, or other physiological response, and to cause the trigger signal to be generated. A peak detected by such a computer algorithm is shown by the circle in FIG. 5, thereby detecting an MER in the user of the pump 100.

The trigger signal may comprise an electrical signal which is sent to the breast pump 100 through an electrical wire 180 which connects the control unit 220 of the sensing unit 200 to a control unit 152 of the breast pump 100. Alternatively, the trigger signal may be sent to the control unit 152 of the breast pump 100 wirelessly using a known communication protocol such as Bluetooth. The control unit 152 of the breast pump 100 may be located in the head unit 151 and may be configured to supply input signals to the actuator 150 and/or the drive mechanism 170 for varying the operation of the breast pump 100 between the different operational modes.

Figure 6:
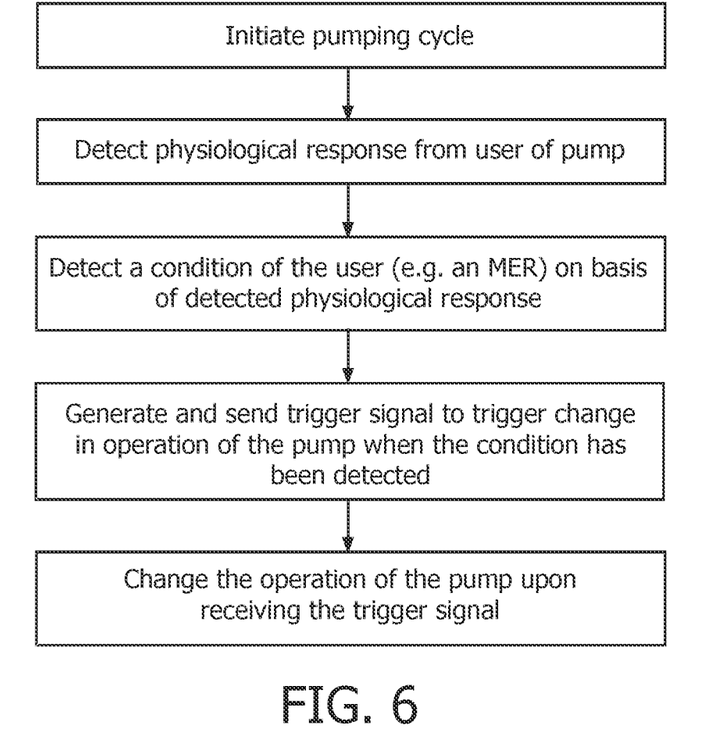
FIG. 6 is a flow diagram of a series of events which may take place when changing the operation of a breast pump in dependence of a detected physiological response of the user of the pump.

For example, referring to FIG. 6, a user of the breast pump 100 may initiate a pumping cycle of the breast pump 100 by pressing a "start" button on the head unit 151. In response to the "start" button being pushed, the control unit 152 of the breast pump 100 may be configured to cause the breast pump 100 to operate in a first mode by providing an input signal to the actuator 150 to instruct the actuator 150 to begin moving the diaphragm 140 upwards and downwards. The first mode may comprise the let-down mode, in which the frequency of the diaphragm cycle may be relatively high and the amplitude of the diaphragm cycle may be relatively low. This causes a relatively fast but soft pumping action to be exerted on the breast tissue, which is designed to provide a stimulation effect that accurately mimics the initial stages of a natural feeding action in order to instigate an MER. The occurrence of an MER is detected in the control unit 220 of the sensing unit 200, which generates and sends a trigger signal to the control unit 152 of the breast pump 100 indicating that an MER has occurred. Upon receiving the trigger signal, the control unit 152 in the breast pump 100 may be configured to switch the operation of the breast pump 100 to a second mode, for example comprising the expression mode, by inputting a switching instruction to the actuator 150 and/or driving mechanism 170. Upon receiving the switching signal, the actuator 150 and/or driving mechanism 170 is configured to alter the operation of the breast pump 100 to the second mode. For example, if the second mode comprises the expression mode, the frequency of the diaphragm cycle may be reduced whilst the amplitude of the diaphragm cycle is increased. This causes a slower, more forceful pumping action to be exerted on the breast tissue. The resulting stimulation effect encourages milk to be expressed from the nipple of the breast.

The automatic transition between the first mode and the second mode means that a user of the breast pump 100 is not required to provide any user input following the initial activation of the pumping action. The breast pump 100 may operate automatically until the desired quantity of milk has been expressed from user's breast. This is desirable because it is known that an MER is most likely to occur when the user of a breast pump is fully relaxed, which is unlikely to be the case when the user is required to concentrate on operating the breast pump 100.

In a variation on the example described in the preceding two paragraphs, the first mode may comprise the relaxation mode, in which one or more optional lights and/or loudspeakers in the sensing means 200 may be respectively configured to output soothing light and sounds to the user of the breast pump 100. The sensing unit 200 may be configured to vary the output of the light and sounds in response to the physiological conditions detected from the user. Once it is detected by the control unit 220 that the user of the pump 100 is in a relaxed state, the sensing unit 200 may generate and send a trigger signal to the control unit 152 of the breast pump 100 indicating that the user is in a relaxed state. Upon receiving the trigger signal, the control unit 152 in the breast pump 100 may be configured to switch the operation of the breast pump 100 to a second mode, for example comprising the let-down mode, by inputting a switching instruction to the actuator 150 and/or driving mechanism 170. Upon receiving the switching signal, the actuator 150 and/or driving mechanism 170 is configured to alter the operation of the breast pump 100 to the second mode.

A number of specific examples of the sensing unit 200 are described below. In these examples, when the breast pump funnel 110 is located against the skin tissue of a breast of the user during use of the pump 100, at least one sensor 210 of the sensing unit 200 is configured to contact with the skin tissue of a part of the user's body other than the breast tissue. More specifically, in the examples below, at least one sensor 210 is configured to contact with the skin tissue of a hand or wrist of the user of the breast pump 100 to detect physiological responses of the user. However, the sensor 210 may alternatively be configured to contact with the skin tissue of an ankle or foot of the user of the pump 100 to detect the physiological response. It is advantageous that such physiological measurements are taken from the skin tissue on hands, wrists or feet because it is those parts of the body which provide the best indication of skin conductance, which can be measured to determine a GSR and, in turn, to detect a condition of the user such as an MER. These parts of the body are also remote from the breast region and the associated milk flow, and so can safely be used to detect an MER without the need to sterilize the sensing equipment before use. It will be appreciated, however, that it is not essential that the sensing unit comprises a sensor 210 configured to contact the skin tissue of one of the aforementioned body parts. This is particularly the case if other types of response other than electro-dermal responses are used to detect a condition of the user.

Figure 7:
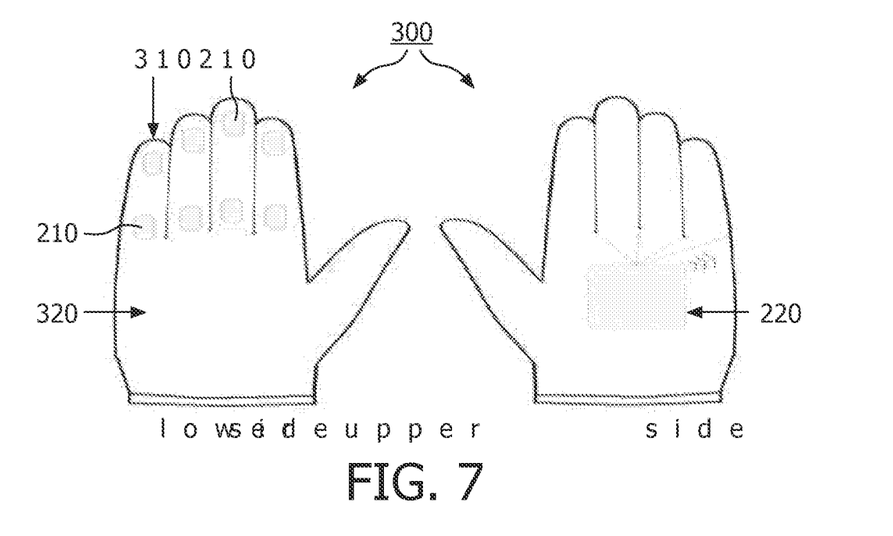
FIG. 7 is an illustration of a glove comprising a sensing unit for sensing a physiological response of a user of a breast pump.

Referring to FIG. 7, the sensing unit 200 may be comprised in a glove 300 to be worn by a user of the breast pump 100 during use. At least one physiological sensor 210 may be located such that it contacts with the skin tissue of a hand of the user when the hand is inserted into the glove 300. For example, the physiological sensor 210 may be located in at least one of a plurality of finger receptacles 310 in the glove 300. Further physiological sensors 210 may be provided in one or more of the other finger receptacles 310 of the glove 300, for example in each of the finger receptacles 310. Physiological sensors 210 may also be provided in the interior of a palm portion 320 of the glove 300.

The control unit 220 may be provided either internally or externally to the glove 300. For example, the control unit 220 may be secured to an interior or external surface of a top side of the glove 300, whilst the physiological sensors 210 are secured to an interior surface of a bottom or palm side of the glove 300 in order to contact the skin tissue of an inserted hand. The control unit 220 may be electrically connected to each of the sensors via electrical wires extending through the fabric of the glove 300.

Figure 8:
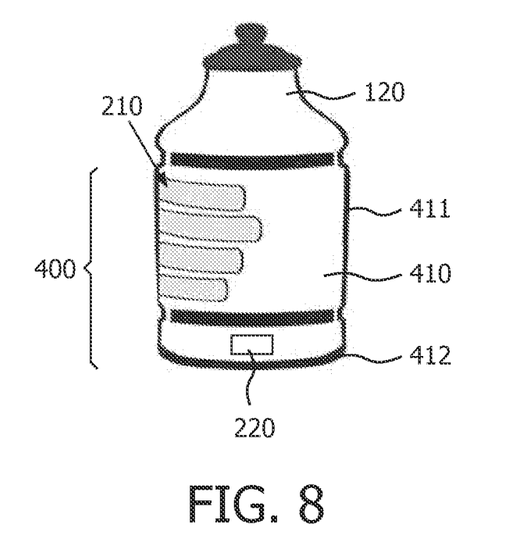
FIG. 8 is an illustration of a holding unit for sensing a physiological response of a user of a breast pump. The holding unit is shown holding a container of the breast pump.

Referring to FIG. 8, the sensing unit 200 may instead be comprised in a holding unit 400 for the breast pump 100. For the purposes of clarity, the holding unit 400 is shown in FIG. 8 as holding only a container 120 of the breast pump 100. However, it will be appreciated that the holding unit 400 is capable of supporting the whole breast pump 100 when the pump 100 is screwed together. The holding unit 400 may, for example, comprise a cage 410 having side walls 411 adapted to fit around a circumferential surface of the container 120 of the breast pump 100, and a base 412 adapted to support the base of the container 120. The cage 410 may further comprise a handle to allow a user of the breast pump 100 to grip the holding unit 400 and thereby support the breast pump 100 against the breast during the expression of milk.

As shown in FIG. 8, at least one physiological sensor 210 may be located on an external surface of the holding unit 400, for example on one or more of the side walls 411, base 412 or handle such that the sensor 210 contacts with the skin tissue of the user's hand when the user grips the holding unit 400. In one example, sensors 210 are provided on each of the side wall 411, base 412 and handle of the cage 410. The sensors 210 may be provided in depressed regions on the exterior of the cage 410 which are shaped to fit the fingers of an adult female. This will encourage a user of the breast pump 100 to place her fingers directly over the top of the sensors 210 and thereby ensure a good contact between the skin tissue of the user's hand and the sensors 210. The control unit 220 may be provided at any convenient location on the holding unit 400, for example on the side wall 411 of the cage 410.

Figure 9:
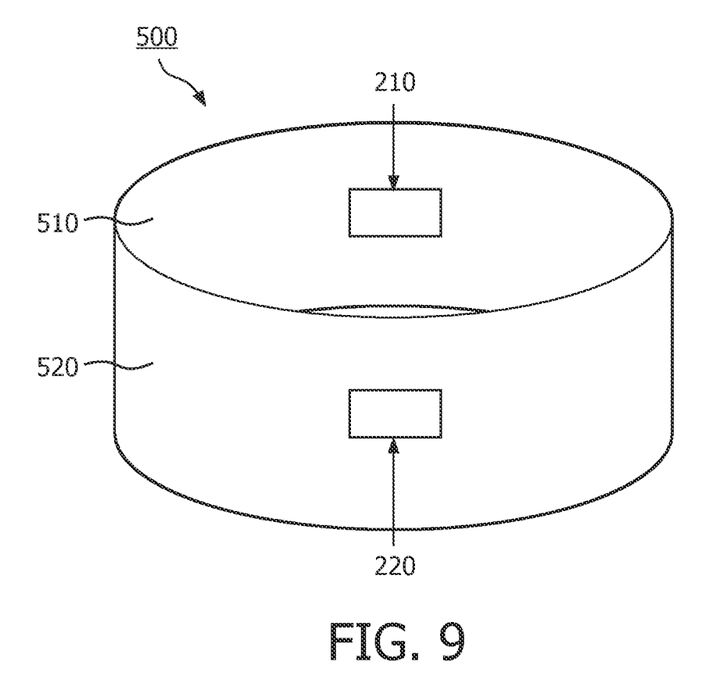
FIG. 9 is an illustration of a wrist or ankle bracelet for sensing a physiological response of a user of a breast pump.

Referring to FIG. 9, the sensing unit 200 may be comprised in a wrist band or bracelet 500 to be worn by a user of the breast pump 100 during use. At least one physiological sensor 210 may be located such that it contacts with the skin tissue of a hand or wrist of the user when the band or bracelet 500 is worn by the user. If the band or bracelet 500 is worn around the ankle or foot, the at least one physiological sensor 210 may be located such that it contacts the skin tissue of the ankle or foot of the user.

Referring to FIG. 9, the at least one physiological sensor 210 may be located on an inner face 510 of the band or bracelet 500 such that it is configured to contact the skin tissue of the user when the band or bracelet 500 is worn. The control unit 220 may be provided on either the inner face 510 or outer face 520 of the bracelet 500. Alternatively, the control unit 220 may be embedded in the band or bracelet 500 to protect it from damage. The control unit 220 may be electrically connected to each of the sensors via electrical wires extending through or across the material of the band or bracelet 500.

Alternatively, the sensing unit 200 may be comprised in the container 120 of the breast pump 100 itself. For example, at least one physiological sensor 210 may be located on an external surface of the container 120, for example on one or more of the side walls or base of the container 120 such that the sensor 210 contacts with the skin tissue of the user's hand when the user grips the container 120 during use of the breast pump 100. In one example, sensors 210 are provided on each of the side walls and base. The sensors 210 may be provided in depressed regions on the exterior of the container 120 which are shaped to fit the fingers of an adult female. This will encourage a user of the breast pump 100 to place her fingers directly over the top of the sensors 210 and thereby ensure a good contact between the skin tissue of the user's hand and the sensors 210. The control unit 220 may be provided at any convenient location on the container 120, for example on a side wall of the container 120.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein the sensing unit is located in a sock and configured to detect physiological responses from the skin tissue of a foot, or in a wrist or ankle band and configured to detect physiological responses from the skin tissue on a wrist or ankle.

Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to an advantage. A computer program may be stored/distributed on a suitable medium, such as an optical storage medium or a solid-state medium supplied together with or as part of other hardware, but may also be distributed in other forms, such as via the Internet or other wired or wireless telecommunications systems. Any reference signs in the claims should not be construed as limiting the scope.

The invention claimed is:

1. An apparatus comprising:
   a sensing unit comprising a physiological sensor configured to detect a physiological response from a user of a breast pump and to trigger a change in an operation of the breast pump from a first stimulation mode from among any one of a plurality of first stimulation modes to a second stimulation mode from said plurality of first stimulation modes in dependence of the detected physiological response which occurs during a first stimulation mode, wherein the sensing unit is located separately from a funnel of the breast pump,
   the sensing unit further comprising a control unit coupled to the sensing unit, configured to receive signals from the sensing unit and analyze the signals to determine one or more physiological responses of the user, the control unit being further configured to compare the physiological responses determined via the sensing unit with stored physiological responses, and,
   wherein the apparatus is configured to operate the breast pump in more than one stimulation mode simultaneously.

2. An apparatus according to claim 1, wherein when the funnel of the breast pump is located against the breast of the user, the sensing unit is configured to detect said physiological response from a body part of the user other than the user's breast.

3. An apparatus according to claim 1, wherein the sensing unit is configured to detect a milk ejection reflex on the basis of the detected physiological response.

4. An apparatus according to claim 3, wherein the sensing unit is configured to trigger a change in the operation of the breast pump from a let-down mode to an expression mode in response to detecting a milk ejection reflex.

5. An apparatus according to claim 1, wherein the sensor is an electrodermal sensor configured to detect said response from skin tissue of the user of the breast pump.

6. An apparatus according to claim 1, wherein the physiological response is a galvanic skin response.

7. An apparatus according to claim 1, wherein the apparatus further comprises a glove in which the sensor is located.

8. An apparatus according to claim 7, wherein the glove comprises at least one finger receptacle and the sensor is located in the at least one finger receptacle to contact skin tissue of a hand of the user when inserted into the receptacle.

9. An apparatus according to claim 1, comprising a bracelet on which the sensor is located.

10. An apparatus according to claim 9, wherein the sensor is located at an exterior of the bracelet to contact the skin tissue of the user when wearing the bracelet.

11. An apparatus according to claim 9, further comprising said breast pump, the breast pump being configured to change its operation in response to receiving a signal from the sensing unit.

12. A method for controlling the operation of a breast pump, comprising:

detecting, by at least one physiological sensor of a sensing unit, signals indicative of one or more physiological responses from a user of the breast pump, transmitting the one or more signals from the at least one physiological sensor to a control unit of the sensing unit, analyzing the signals received in the control unit to determine the one or more physiological responses of the user of the breast pump, the responses being detected from a body part of the user of the breast pump other than the user's breast, and comparing the one or more physiological responses with stored physiological responses, stored in a storing unit of the sensing unit, to determine if the one or more physiological responses corresponds to a milk ejection reflex of the user, triggering a change in an operation of the breast pump from a first stimulation mode from among any one of a first plurality of stimulation modes to a second stimulation mode from among said plurality of stimulation modes in dependence of the detected physiological response which occurs during said first stimulation mode, and wherein the breast pump may be operated in more than one stimulation mode simultaneously, and wherein the sensing unit is located separately from a funnel of the breast pump.

13. A method according to claim 12, wherein detecting the physiological response occurs whilst a funnel of the breast pump is located against a breast of the user of the pump.

14. A method according to claim 12, comprising detecting a milk ejection reflex on the basis of the detected physiological response.

* * * * *